US005641762A

United States Patent [19]
Pierce, Jr. et al.

[11] Patent Number: 5,641,762
[45] Date of Patent: Jun. 24, 1997

[54] BONE TARGETED INHIBITORS OF CARBONIC ANHYDRASE

[75] Inventors: William M. Pierce, Jr., Louisville, Ky.; Leonard C. Waite, Corydon, Ind.

[73] Assignee: Research Corporation Technologies, Inc., Tucson, Ariz.

[21] Appl. No.: 270,846

[22] Filed: Jul. 1, 1994

Related U.S. Application Data

[63] Continuation of Ser. No. 909,138, Jul. 6, 1992, abandoned, which is a continuation of Ser. No. 514,638, Apr. 25, 1990, abandoned, which is a continuation-in-part of Ser. No. 274,697, Nov. 15, 1988, abandoned, which is a continuation of Ser. No. 730,873, May 3, 1985, abandoned.

[51] Int. Cl.$^6$ .................. C07F 9/6539; C07D 285/12; A61K 31/65; A61K 31/675
[52] U.S. Cl. .............. 514/80; 514/92; 514/152; 548/112; 548/118; 548/119; 552/203
[58] Field of Search .................. 548/112, 118, 548/119; 552/203; 514/80, 92, 152

[56] References Cited

U.S. PATENT DOCUMENTS

| | | | |
|---|---|---|---|
| 4,687,767 | 8/1987 | Bosies | 514/89 |
| 4,876,248 | 10/1989 | Breliere | 514/108 |

FOREIGN PATENT DOCUMENTS 669610  12/1965  Belgium.

*Primary Examiner*—Robert Gerstl
*Attorney, Agent, or Firm*—Scully, Scott, Murphy & Presser

[57] ABSTRACT

The present invention relates to novel compounds useful for the treatment and prophylaxis of degenerative bone disorders and to the preparation thereof. These compounds are particularly characterized by two active moieties, the first of which possesses "bone-seeking" affinity and the second which is an inhibition of the enzyme carbonic anhydrase and/or an inhibitor of bone resorption. The novel compounds of this invention can be administered as pharmaceutically acceptable compositions and in convenient dosage unit form in a method for the treatment and prophylaxis of degenerative bone disorders.

21 Claims, 13 Drawing Sheets

A = DRUG BOUND TO HYDROXYAPATITE
B = DRUG NOT BOUND TO HYDROXYAPATITE
C = DRUG ELUTED BY 1.0 M PHOSPHATE
D = DRUG ELUTED BY 2.0 M PHOSPHATE
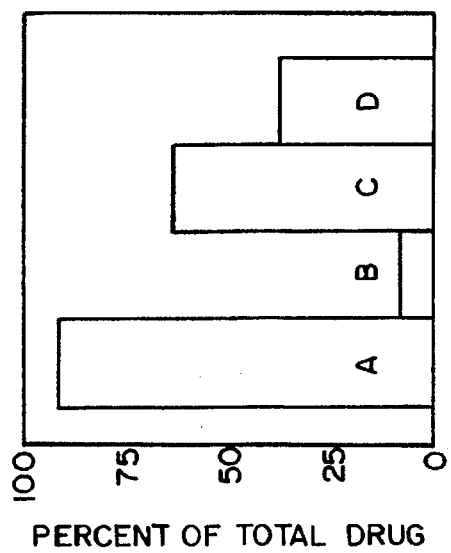
FIG.1A ACETAZOLAMIDE
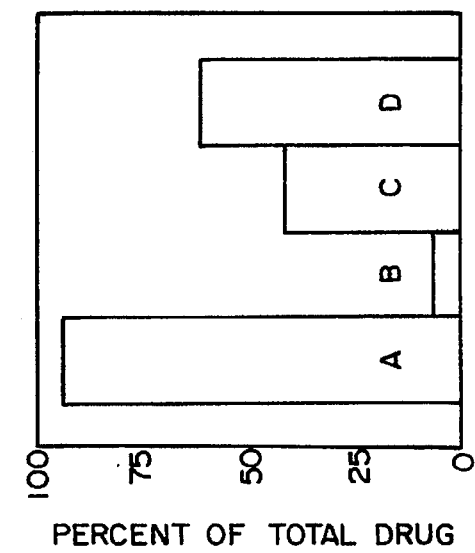
FIG.1B TETRACYCLINE
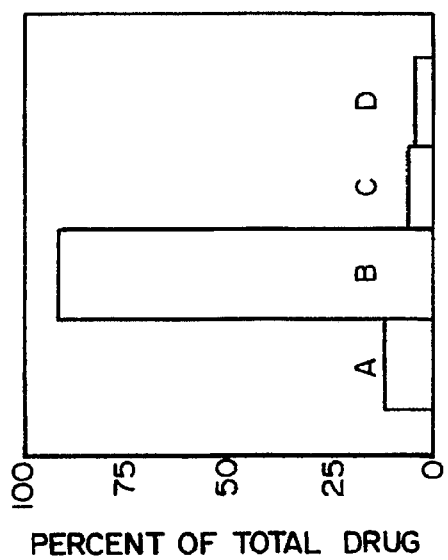
FIG.1C AAOEt
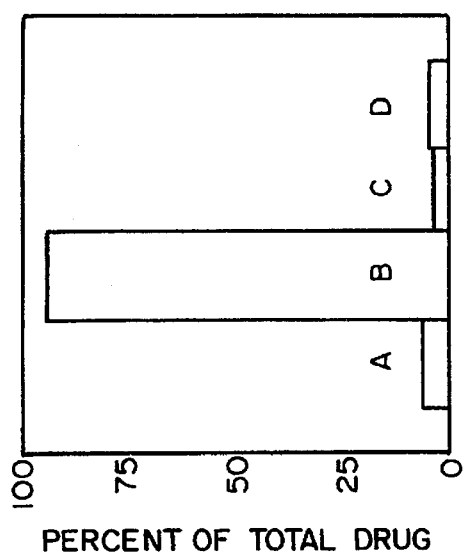
FIG.1D WP-120384

% Total $^{45}$Ca Released (6 day cultures)

BONE TARGETED INHIBITORS OF CARBONIC ANHYDRASE

CROSS REFERENCE TO PRIOR APPLICATIONS

This is a continuation of application Ser. No. 909,138 filed on Jul. 6, 1992, now abandoned, which is a File-Wrapper continuation of Ser. No. 514,618, filed on Apr. 25, 1990, now abandoned, which is a continuation-in-part of Ser. No. 274,697, filed on Nov. 15, 1988, now abandoned, which is a File-Wrapper continuation of Ser. No. 730,873 filed on May 3, 1985, now abandoned.

BACKGROUND OF THE INVENTION

The present invention relates to novel compounds useful in the treatment and prophylaxis of degenerative bone disorders and to a method of their preparation. More specifically, the present invention contemplates novel compounds which are characterized by two active moieties. The first molecular domain possesses "bone-seeking" affinity while the second moiety is a specific inhibitor of the enzyme carbonic anhydrase and/or an inhibitor of bone resorption. The compounds of this invention can be administered alone or as pharmaceutically acceptable compositions and in convenient unit dosage form in a method for the treatment and prophylaxis of degenerative bone disorders.

Bone is a dynamic tissue, consisting of cells in a protein matrix, upon which is superimposed a crystalline structure of various calcium salts. Obviously, the bony skeleton serves as the rigid support for the body. In addition, bone is an organ which responds to hormones. In response to the parathyroid hormone (PTH), bone cells are able to solubilize the calcium salts in bone for use elsewhere in the body. This is a normal regulatory function of bone.

Diseases of excessive bone degeneration exist, including Paget's disease of bone and osteoporosis. The mechanisms are not well understood. In addition, the treatments available are, in general, ad hoc combinations of endocrine and mineral treatments which are often unsuccessful. Clinical osteoporosis is found in approximately 25% of post-menopausal women, and subclinical osteoporosis, which is responsible for untold numbers of bone fractures in elderly women, is far more widespread.

The mechanisms by which bone cells break down bone have been extensively studied but are not clearly defined. One likely scenario is that resorption is caused by the secretion, by bone cells, of acid and photeolytic enzymes. For these enzymes to have their effect, it is likely that the tissue must be decalcified first. Thus, the initiating step is thought to be the acidification of the internal environment of bone, which is responsible for decalcification. One such acid, which has been implicated for many years in these processes, is carbonic acid.

Assuming carbonic acid, which is generated by the enzyme carbonic anhydrase, is involved in bone resorption, then administration of a drug which inhibits carbonic anhydrase should inhibit the liberation of calcium from bone in response to PTH.

This is indeed the case, as was first demonstrated in mammals by Waite, et al. in the publication entitled, "Inhibition of Bone Resorption by Acetazolamide in the Rat", Endocrinology, 87: 1129(1970). One of the models used was the Induced Secondary Hyperparathyroid Rat (ISHR). ISHR were prepared by surgical ligation of the renal arteries. In the rat, the kidney is responsible for the metabolism of citrate. Upon ligation of the renal arteries, blood citrate concentration increases. Citrate chelates calcium and, while total calcium concentration is not affected by this binding, the amount of ionized calcium declines. This drop in plasma ionized calcium is the signal for the release of PTH. PTH, once released, signals bone to begin the resorptive process.

As one would predict, in the ISHR this increased release of PTH leads to an increase in total plasma calcium concentration. Administration of the carbonic anhydrase inhibitor acetazoramide to ISHR completely inhibits this response.

Using classic endocrine ablation/replacement studies, it has been shown that this effect is indeed due to a response to PTH. If the ISHR rat has the parathyroid glands removed, the expected increase in plasma calcium concentration is not observed. In this same animal (ISHR without parathyroids) however, administration of PTH evokes the response, while acetazoramide and other heterocyclic sulfonamides (carbonic anhydrase inhibitors) abolish it.

Later work in tissue culture showed that inhibition of PTH-induced resorption by acetazolamide is due to a direct interaction at the level of bone ("Carbonic Anhydrase and Bone Remodeling: Sulfonamide Inhibition of Bone Resorption in Organ Culture", Minkin and Jennings, Science, (June 1970)).

These studies would lead one to suggest that acetazolamide would be useful as an inhibitor of bone resorption. However, when one administers acetazolamide or other heterocyclic sulfonamide carbonic anhydrase inhibitors to normal animals, no change in plasma calcium concentration is observed. It has been demonstrated that the reason for this is that acetazolamide, while inhibiting calcium dissolution from bone due to the PTH response, also causes a systemic acidosis which of itself increases the shift of mineral from bone to blood. These two competing effects mask one another. (See, "Acidosis Inhibits the Hypocalcemic Effect of Acetazolamide", Lineberry and Waite, Pharmacol. Exp. Ther., 211: 452 (1979)).

Since these original studies several other factors relative to bone resorption have been determined. For example, the following have subsequently been observed: heterocyclic sulfonamides such as acetazolamide which inhibit carbonic anhydrase also inhibit bone resorption; these sulfonamides have both effects (carbonic anhydrase inhibition and inhibition of bone resorption) at the same concentrations; heterocyclic sulfonamides which do not inhibit carbonic anhydrase do not inhibit bone resorption; the sulfonamides also inhibit the bone resorptive effects of large doses of Vitamin D; and since other parameters of bone metabolism are not affected by the sulfonamides, this is not a simple toxicity to bone cells. These studies have been accomplished over a period of approximately 15 years and have involved both in vivo and in vitro work.

In view of these prior studies and other additional information recently derived herein, the compounds and methods of the present invention were contemplated in an effort to confer specificity on a novel inhibitor which would be localized specifically in bone so that it would have little or no effect on soft tissue carbonic anhydrase and would be available on site thereby overcoming the inadequacies which presently characterize known regiments for use of carbonic anhydrase inhibitors.

SUMMARY OF THE INVENTION

It is therefore one object of the present invention to provide novel compounds and their pharmaceutically acceptable compositions which are useful in the treatment and prophylaxis of degenerative bone disorders.

Another object of this invention is to provide a method of preparation for these novel compounds.

A further object of the present invention is to provide a method of treatment and prevention of degenerative bone disorders.

These and other objects are achieved by providing novel compounds which are particularly characterized by two active moieties. The first of these "molecular domains" possesses "bone-seeking" affinity while the second is a specific inhibitor of the enzyme carbonic anhydrase and/or an inhibitor of bone resorption. Optionally, a "bridging" agent can be incorporated into the compounds of the present invention in order to separate the two "active" moieties thereby improving their respective efficacy, i.e., preventing cyclization of these active constituents and avoiding deleterious effects caused by steric hinderance. The present compounds can be prepared by contacting the bone-seeking moiety constituent with the inhibitor constituent for a time and under conditions necessary for the preparation of these novel compounds, conveniently termed "osteostats".

Moreover, the compounds of this invention can be administered alone or in pharmaceutically acceptable compositions in effective amounts sufficient for the treatment and prophylaxis of degenerative bone disorders such as, for example, Paget's disease and osteoporosis.

BRIEF DESCRIPTION OF THE DRAWINGS

FIG. 1 is a graphic illustration depicting the relative binding of acetazolamide, tetracycline, acetazolamide-adipate-ethyl ester (AAOEt) and tetracycline internally active acetazolamide (TIA or WP-120384).

DETAILED DESCRIPTION OF THE INVENTION

Figure 2:
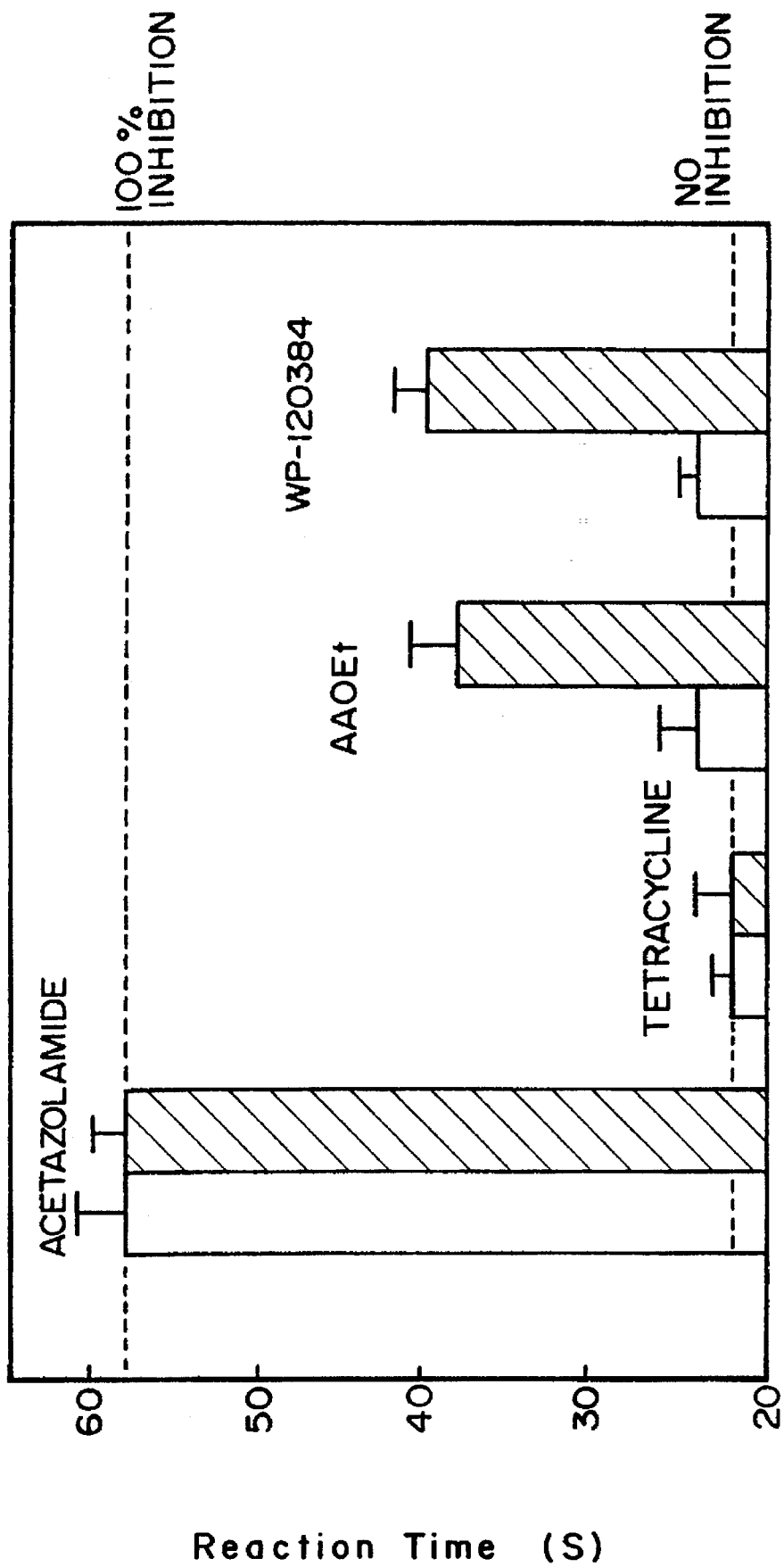
FIG. 2 is a graphic illustration depicting the results of an assay for carbonic anhydrase activity in the presence of acetazolamide, tetracycline, AAOEt and TIA.

In accordance with the present invention, novel compounds herein called "osteostats" are provided which are useful for the treatment and prophylaxis of degenerative bone disorders. These compounds are particularly characterized by two active moieties. The first is a compound which exhibits "bone-seeking" affinity. In this context, "bone-seeking" affinity is defined as having the capability to bind calcium with a tendency to accumulate in bone and to incorporate into its crystal lattice. The second necessary constituent of the present compounds is an inhibitor of the enzyme carbonic anhydrase which catalyzes the reversible hydration of carbon dioxide to carbonic acid (and/or an inhibitor of bone resorption). This reaction, as earlier indicated, has been clearly implicated in the bone resorption process which process is defined as the cell-mediated breakdown of bone.

The compounds of the present invention therefore are the reaction products of a bone-seeking compound, an inhibitor of carbonic anhydrase (and/or inhibitor of bone resorption) and, optionally, a bridging agent.

Compounds which exhibit bone-seeking affinity and which exemplify this moiety of the present compounds are the tetracyclines including, for example, chlortetracycline hydrochloride, demeclocycline hydrochloride, doxycycline, tetracycline, methacycline, oxytetracycline and the like. Other bone-seeking moieties within the scope of the present compounds are the diphosphonates such as, for example, aminohexyldiphosphonate, ethane-1-hydroxy-1,1-diphosphonic acid (EHDP), dichloromethane diphosphonic acid ($Cl_2MDP$), 3-amino-1-hydroxypropane-1,1-diphosphonic acid (AHPDP) and the like. Tetracycline is preferred.

The carbonic anhydrase inhibitors exemplary of this moiety of the present compounds are the imidazoles, imidazole derivatives and the sulfonamides, particularly acetazolamide, methazolamide, ethoxzolamide, benzolamide and the like, acetazolamide being preferred.

Mithramycin is a compound which can be employed in the present invention which exhibits inhibition of bone resorption, but may not be a carbonic anhydrase inhibitor, per se. Nevertheless, its efficacy is within the scope of the present compounds.

Optionally, although preferably, a third constituent can be incorporated between the other "active" moieties of the present compounds. These "bridging agents" merely insure the efficacy of the active moieties, i.e., by assuring that the compound does not cyclize prior to hydrolysis of the compound in vivo and further avoids the detrimental effects of steric hinderance.

Compounds which are useful as bridging agents in the context of this invention are not limited to any specific group and can, for example, be various $C_4$-$C_{20}$ alkylene chains (difunctional) characterized as having one functional end capable of aromatic carbon electrophilic substitution. Representative of such groups are alkyl halides, alcohols, olefins, esters (i.e., facilitating alkylation in the presence of a Lewis acid), acyl halides, carboxylic acids, anhydrides (i.e., facilitating acylation) and the like; and another functional end capable of undergoing an amide forming reaction. Representative of such groups are acids or acid derivatives including, for example, carboxylic acids, anhydrides, acyl halides and the like.

The active moieties, i.e., molecular domains of the "osteostat", can be schematically illustrated as shown below:

The following scheme of preparation is exemplary of the process which can be employed for the preparation of the present compounds:

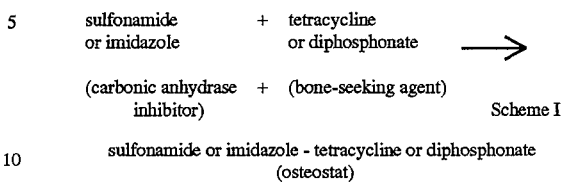

A specific example of preparation is shown in Scheme II.

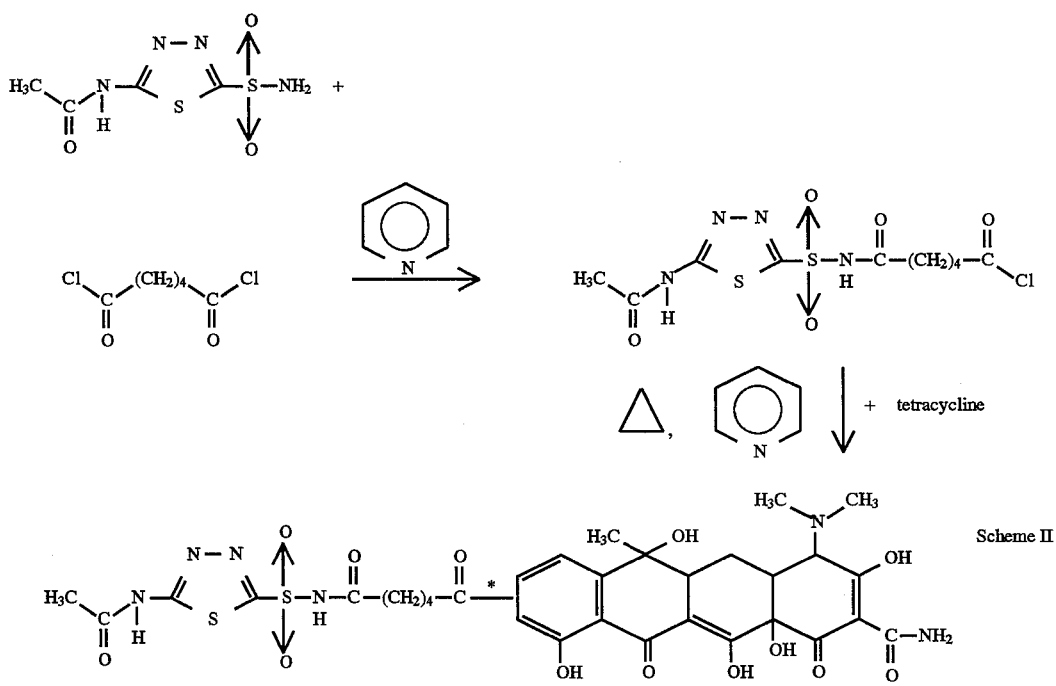

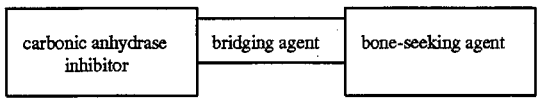

The efficacy of these "osteostats" can be facilitated immediately at the bone site, i.e., having the active sites of both moieties available (not a pro-drug). Preferably, however, the efficacy of these "osteostats" can be facilitated stepwise, first by the bone-seeking moiety which affinity localizes the compound at the bone site. Internally compounded, the osteostat can therefore be a pro-drug, i.e., the active site of the inhibitor is internal in the compound and not immediately available, and will exhibit no initial activity. However, when subjected to the enzymatic hydrolytic conditions occuring at the bone site, i.e., by the production of carbonic acid, the carbonic anhydrase inhibitor will be released in a second step in response to the very process which it is designed to inhibit. This action reflects an ideal feedback system and is elicted only in response to the specific need.

The compounds of the present invention may contain one (1) or more asymmetric carbon atoms and may exist in racemic and optically active forms. Depending upon the substituents, the present compounds may form addition salts as well. All of these forms are contemplated to be within the scope of this invention.

The present compounds obviously exist in stereoisomeric forms and the products obtained thus can be mixtures of the isomers, which can be resolved. Alternatively, by selection of specific isomers as starting compounds, the preferred stereoisomer can be produced.

In a preferred embodiment, the following compounds are contemplated for use in the present invention: tetracycline-internally-active acetazolamide (TIA), tetracycline-internally-active ethoxzolamide (TIE), tetracycline active acetazolamide, tetracycline active ethoxzolamide Δ-1, tetracycline active ethoxzolamide Δ-2, and aminohexyldiphosponate-active-acetzolamide.

The active ingredients of the therapeutic compositions and the compounds of the present invention exhibit excellent activity in the treatment and prevention of degenerative bone disorders when administered in amounts ranging from about 0.1 mg to about 10 mg per kilogram of body weight per day. A preferred dosage regimen for optimum results would be from about 1 mg to about 10 mg per kilogram of body weight per week, and such dosage units are employed that a total of from about 7 mg to about 700 mg of the active compound for a subject of about 70 kg of body weight are administered in a 24-hour period. This dosage regimen may be adjusted to provide the optimum therapeutic response and is preferably administered 2 times a day in dosages of about 50 mg per administration. For example, several divided doses may be administered daily of the dose may be proportionally reduced as indicated by the exigencies of the therapeutic situation. A decided practical advantage is that the active compound may be administered in an convenient manner such as by the oral, intraveneous, intramuscular or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 5% of active compound. The percentage of the compositions and preparations may, of course, be varied and may conveniently be between about 1 to about 10% of the weight of the unit. The amount of active compound in such therapeutically useful compositions is such that a suitable dosage will be obtained. Preferred compositions or preparations according to the present invention are prepared so that an oral dosage unit form contains between about 5 and 500 mg of active compound.

The tablets, troches, pills, capsules and the like may also contain the following: A binder such as gum tragacanth, acacia, corn starch or gelatin; excipients; disintegrating agents such as corn starch, potato starch, alginic acid and the like; lubricants; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorcbutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 0.1 to about 1000 mg, with from about 5 to about 500 mg being preferred. Expressed in proportions, the active compound is generally present in from about 1 to about 100 mg/ml of carrier. In the case of compositions containing supplementary active ingredients, the dosages are determined by reference to the usual dose and manner of administration of the said ingredients.

For a better understanding of the present invention together with other and further objects, reference is made to the following description and example.

EXAMPLES

PROTOCOLS

As discussed above, carbonic anhydrase (CA) is indicated as playing a functional role in bone resorption. The examples described herein detail the synthesis, chemical characterization and pharmacological testing of the members of a family of compounds which are bone-targeted carbonic anhydrase inhibitors.

This includes:

a) Synthesis of candidate bone-targeted CA inhibitors;

b) Physicochemical studies, conducted to verify successful synthesis, assess some physicochemical properties and to develop procedures for quantitative analysis of these compounds;

c) Assessment of two key biochemical properties which these compounds must exhibit:
  1. a high affinity for bone mineral; and
  2. the ability to either serve as inhibitors of CA or to serve as prodrugs which gives rise to CA inhibitors under bone resorptive conditions; and d) Assessment of biological activity in:
  1. an in vitro model; and
  2. two in vivo models.

Six compounds will be discussed in Examples I–VI:

(I) Tetracycline internally active acetazolamide [TIA], also designated as WP-120384;

(II) Tetracycline internally active ethoxzolamide [TIE], also designated as WP-021786;

(III) Tetracycline active acetazolamide [TAA], also designated as KK-020287;

(IV) Tetracycline active ethoxzolamide Δ1 [TAE-1], also designated as WP-050686;

(V) Tetracycline active ethoxzolamide Δ2 [TAE-2], also designated as WP-020387;

(VI) Aminohexyldiphosphonate-active-acetazolamide [PAA], also designated as WP-050188.

The designations refer to laboratory log numbers. Compounds designated as "acetazolamide derivatives" are derived from the thiadiazole family and "ethoxzolamide derivatives" are derived from the benzothiazole family. "Active" indicates an active configuration (primary sulfonamide) wherein "activity" as a carbonic anhydrase inhibitor is immediately available. "Internally active" indicates that the active site of the inhibitor is internal in the compound and not immediately available, and will exhibit no initial activity. However, when subjected to enzymatic hydrolytic conditions occurring at the bone site, i.e., by the production of carbonic acid, the "internally active" carbonic anhydrase inhibitor will be released in a second step in a feedback system, and is elicited only in response to the specific need for this inhibitor. TIA has also been designated in the literature as WP-1 (*Proc. Soc. Exp. Biol. Med.*, 186: 96–102 (1987)).

MATERIALS AND METHODS a) Synthesis. Synthesis of these compounds is discussed below along with detailed consideration of each compound as set forth in Examples I–VI.

b) Physicochemical Characterization. Melting points were determined using a Fisher-Johns apparatus with a heating rate of 2 degrees (C) per minute. Infrared spectra were obtained using a Perkin-Elmer spectrometer (Perkin Elmer, Norwalk, Conn.) and KBr discs, scanning from 680–4000 $cm^{-1}$. Ultraviolet-visible spectroscopy was performed using 1 cm quartz cuvettes and a Cary 19 spectrophotometer (Varian Associates, Palo Alto, Calif.). Spectra were obtained on $10^{-6}M$ solutions in 0.1N HCl and 0.1N NaOH, scanning from 600–190 nm.

Chromatographic characterization was accomplished using hydroxyapetite (HA) chromatography, silica gel thin layer chromatography and high performance reverse phase liquid chromatography (HPLC) with the following characteristics:

Column: LC-18-DB (Supelco)/25 cm/5 um particles.

Mode: Isocratic

Mobile phase: 9% tetrahydrofuran/9% $CH_3CN$/1% $CH_3OH$/81% 5 mM sodium phosphate, pH=2

Flow rate: 1 ml/min

Temperature: ambient

Detection: UV-visible absorbance 210–500 nm (photodiode array scanning)

This mode of analysis served simultaneously as a qualitative analytic procedure (full UV-vis spectrum) as well as providing a quantitative estimate of drug concentration.

c) Biochemical Properties

To function as a bone-targeted carbonic anhydrase inhibitor, these compounds must have two key biochemical properties, i.e., they must (1) bind to bone mineral with an affinity far greater than for any other tissue, and (2) serve as inhibitors of carbonic anhydrase or under acid hydrolyric conditions must yield an inhibitor of CA. Thus, these examples demonstrate, in defined chemical systems, the efficacy of the compounds of Examples I–VI with respect to each of these properties.

A—Binding to Hydroxyapatite

For these studies, $10^{-5}M$ aqueous solutions of the various test agents were added to a slurry of hydroxyapatite (HA), the principle mineral constituent of bone. After a 30 minute incubation, HA was separated by centrifugation and treated with 1.0M phosphate buffer (pH=7) or 2.0M phosphate buffer (pH=7). Percentage of total drug bound and eluted was determined using UV-visible spectrophotometry.

B—Carbonic Anhydrase Inhibition

A modification of the micromethod of Maven, *J. Pharmacol. Exp. Ther.* 130: 26–29 (1960) was used to assess carbonic anhydrase activity and inhibition. In essence, a bicarbonate solution was incubated at 0° C. in a vessel which was constantly bubbled with $CO_2$. A pH indicator (phensulfophthalein) was included. The dependent variable was the amount of time required to achieve color change (addition of bicarbonate is defined as time zero). Addition of carbonic anhydase decreased reaction time. Further addition of enzyme inhibitors extended reaction time back to control values. This technique was useful for quantitative analyses of CA inhibitor concentrations, with a lower limit of sensitivity of $10^{-7}M$ and a precision of ±3% at this lower. (Acetazolamide concentration was also determined using the HPLC method described above.)

d) Assessment of Biological Activity

1) In vitro activity

To test the biological activity of TIA and to do so directly at the level of the proposed target organ, experiments were conducted using an in vitro bone organ culture system.

Essentially, fetal or neonatal rat calvaria were excised and cultured in serum supplemented BGJb medium (GIBCO) containing HEPES buffer (hydroxyethylpiperazine-ethanesulfonate), penicillin and streptomycin. Bone samples were individually incubated in sterile multi-well plates at 37° C./100% relative humidity/95:5 air:$CO_2$. If appropriate, bone may be radiolabeled by injection of mothers with $^{45}CACl_2$ or pups with tritiated proline.

2) In vivo Activity

1. The Induced Secondary Hyperparathyroid Rat

In order to test the biological activity of these substances, test compounds were injected intraperitoneally into 100 gram female rats. Twenty-four hours later the animals were subjected to bilateral nephrectomy. Animals were bled 4 hours post nephrectomy. Bilateral nephrectomy in rats resulted in an accumulation of citrate in the circulation and a subsequent chelation of ionized calcium. The resulting decline in the concentration of ionized calcium in the blood served as a stimulus for the release of PTH. In animals with functional parathyroid glands, a secondary hyperparathyroidism developed with an ensuing hypercalcemia due to PTH-induced bone resorption. Agents which inhibited bone resorption attenuate this hypercalcemic response.

Although this model has proven useful in other studies of carbonic anhydrase inhibitors and bone metabolism, remaining unknowns included whether: (1) these manipulations influence the rates of synthesis or secretion of PTH, (2) the effect of the loss of renal 25-OH-$D_3$-1-hydroxylase due to nephrectomy is significant (although ligation of the ureters rather than the blood supply yields the same results in similar experiments). Another model (ablation/replacement) was employed to answer these questions, in which the kidneys are intact and the parathyroid glands are excised.

2. Ablation/replacement

Parathyroid hormone was administered to parathyroidectomized rats who received no food for 12 hours before PTH injection, to minimize gut calcium absorption. In an attempt to attenuate the developing increase in plasma calcium, drug was administered 24 hours prior to PTH injection.

EXAMPLE I

TIA (WP-120384)

a) Synthesis

Several isomers were formed, since there are six active hydrogen sites in the molecule (although not of equivalent acidity). The tricarbonyl methane region of the tetracycline molecule is the key region involved in calcium binding, and any modification of this molecular domain yields a product which is not a "bone-seeker." All preparations were purified by either silica gel chromatography or hydroxyapatite chromatography. Purity was assessed by reverse phase chromatography.

The final products were isolated by adsorption to hydroxyapatite (HA). The HA was then washed extensively and then slurried in 2M sodium phosphate (pH=3) and extracted with 1-butanol. The butanolic solution was then taken for rotary vacuum evaporation. Further purification was accomplished using HA or reverse phase chromatography. This scheme selects against any species which would not have a high affinity for bone.

Tetracycline was recrystallized twice, once from methanol, once from dichloromethane. TIA was the product of the condensation of one equivalent each of tetracycline and acetazolamide with adipoyl dichloride (1,6-hexanedioyldichloride). This yielded a hexanedioic acid bridge between the sulfonamide nitrogen of acetazolamide and tetracycline. The second compound, acetazolanide-adipate-ethyl ester (AAOEt), was a similar condensation product of acetazolamide, adipoyl dichloride and ethanol, with a hexanedioic bridge between the sulfonamide nitrogen and the ethyl ester. The chemical structures of tetracycline, AAOEt, and TIA are represented below.

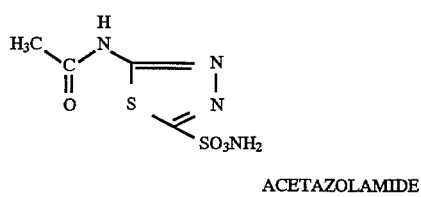

ACETAZOLAMIDE

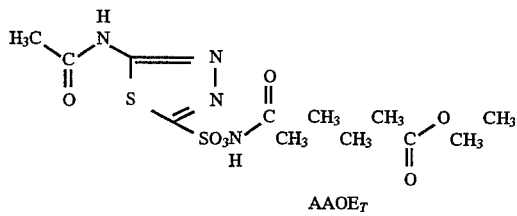

AAOE$_T$

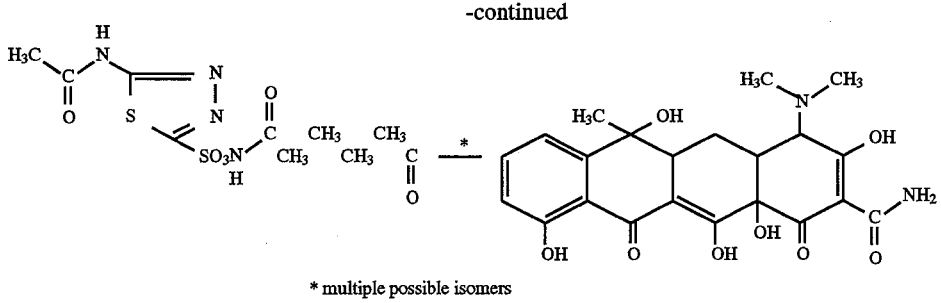

*multiple possible isomers

TIA

Each of these compounds was synthesized in two steps. The first step was the condensation of adipoyl dichloride and acetazolamide. In a 500 ml round bottom flask, 4.44 g (0.02 mol) acetazolamide was slurried in 260 ml pyridine. To this mixture 0.02 mol adipoyl dichloride was added dropwise over a period of two hours. The mixture was stirred at room temperature for 24 hours. The resultant was divided into two portions, and one was taken for synthesis of acetazolamide—adipate—ethyl ester. The remainder was used for synthesis of TIA.

AAOEt was synthesized by adding the above described acetazolamide-adipoyl hemichloride to boiling ethanol and maintaining the solution at reflux for one hour. The solvent was removed under vacuum, and the product was recrystallized from methanol.

TIA was synthesized by adding 4.44 g (0.01 mol) tetracycline to the remaining 0.01 mol (theoretical) acetazolamide—adipoylhemichloride, along with 100 ml dimethylsulfoxide (DMSO) and 20 ml pyridine. The mixture was maintained at 50° C. for 48 hours with stirring. Two hundred ml of water was added to the flask with stirring, and 50 ml of a 15% (v:v) slurry of hydroxyapatite was added. The mixture was then allowed to stir gently overnight at room temperature. Hydroxyapatite was recovered by filtration, and washed three times with 200 ml each hot water, methanol and ethyl acetate and allowed to dry under vacuum at room temperature. The resultant product was then suspended in 1.0M sodium phosphate buffer (pH=7), filtered again and resuspended in 2.0M sodium phosphate (pH=7). This suspension was mixed with 100 ml 1-butanol to extract the final product, which was recovered by stripping the solvent under vacuum. Product yield was 1.2 g (15% of theoretical).

b) Physicochemical Properties

Physicochemical properties of AAOEt and TIA were studied in parallel with those of the parent compounds, acetazolamide and tetracycline (Table 1). Melting ranges were determined, and AAOEt was shown to have a melting range approximately the same as that of acetazolamide. TIA decomposed at 220° C., as does tetracycline. Values derived from the available literature for tetracycline and acetazolamide were listed in brackets throughout Table 1.

TABLE 1

| | Physiochemical Characterization | | | |
|---|---|---|---|---|
| Acetazolamide | Tetracycline | AAOEt | TIA | |
| | Melting Range (°C.) | | | |
| 258–260 [258][a] | dec. 220 [dec. 214][b] | 256–258 | dec. 220 | |
| | IR Spectral Bands (cm$^{-1}$) | | | |
| A 1550 [1548] | A 1580 [1580] | A 1540 | A 1610 | |
| B 1345 [1363] | B 1400 | B 1360 | B 3300 | |
| C 1170 [1167] | C 3300 | C 1270 | C 2060 | |
| | UV Visible Absorbance Maxima (nm) | | | |
| 292 (0.1 N NaOH)[c] | 385 (0.1 N NaOH) | 298 (0.1 N NaOH) | 383, 290 (0.1 N NaOH) | |
| 266 (0.1 N HCl) | 359, 268 (0.1 N HCl) | 264 (0.1 N HCl) | 359, 265 (0.1 N NaOH) | |
| | HPLC Capacity Factor (k')[d] | | | |
| 1.14 | 3.55 | 1.73 | 3.95 | |

[a] [ ] – Values in brackets are literature data.
[b] dec. = decomposes
[c] denotes solvent for spectroscopic analysis
[d] k' is defined as $\frac{Vr - Ve}{Ve}$ where: $Vr$ = Retention volume; $Ve$ = Void volume of the system Spectroscopic data was obtained as well. Infrared and UV-visible major absorbances, consistent with the structures of TIA and AAOEt, are shown in Table 1. In addition, pH-dependent shifts in absorbance of UV-visible light are consistent with the structures for TIA and AAOEt; each manifests the properties of its parent compounds.

Chromatographic data was obtained using the HPLC system described. AAOEt is more lipophilic than is its parent, acetazolamide. TIA was shown to be more lipophilic than either of its parent compounds.

c) Biochemical Properties

1. Binding to hydroxyapatite. Binding of test compounds to hydroxyapatite was studied, and results are shown in FIG. 1. Acetazolamide and AAOEt have no particular affinity for hydroxyapatite; only 19% of acetazolamide and 3% of the AAOEt were bound to hydroxyapatite under these conditions. In contrast, 92% of the TIA and 90% of the tetracycline was bound to hydroxyapatite. Most of the tetracycline was eluted with 1.0M sodium phosphate. TIA was equally or more tightly bound, requiring 2.0M sodium phosphate to achieve elution of most of the TIA.

2. Inhibition of carbonic anhydrase.

Acetazolamide, tetracycline, AAOEt and TIA were all tested for carbonic anhydrase inhibitory activity (FIG. 2). All are tested before and after being subjected to hydrolyric conditions with the final assay concentration being $5 \times 10^{-6}$M. For these experiments, the dependent variable was the amount of time required for acidification of a $CO_2$/bicarbonate buffer system to a defined endpoint. With no additions, the time required was 54±2 s. Addition of purified carbonic anhydrase decreased reaction time to 23±1 s. Finally, test drugs were added to enzyme-containing reaction mixtures, and any increase in reaction time was indicative of enzyme inhibition. Drug vehicles were tested independently to assure that they have no influence on reaction time (FIG. 2).

Acetazolamide was shown to be the only compound which inhibits carbonic anhydrase activity. Following incubation under hydrolytic conditions, acetazolamide solutions derived from AAOEt and TIA each inhibited carbonic anhydrase activity. Tetracycline was without effect.

d) Assessment of Biological Activity

Figure 3:
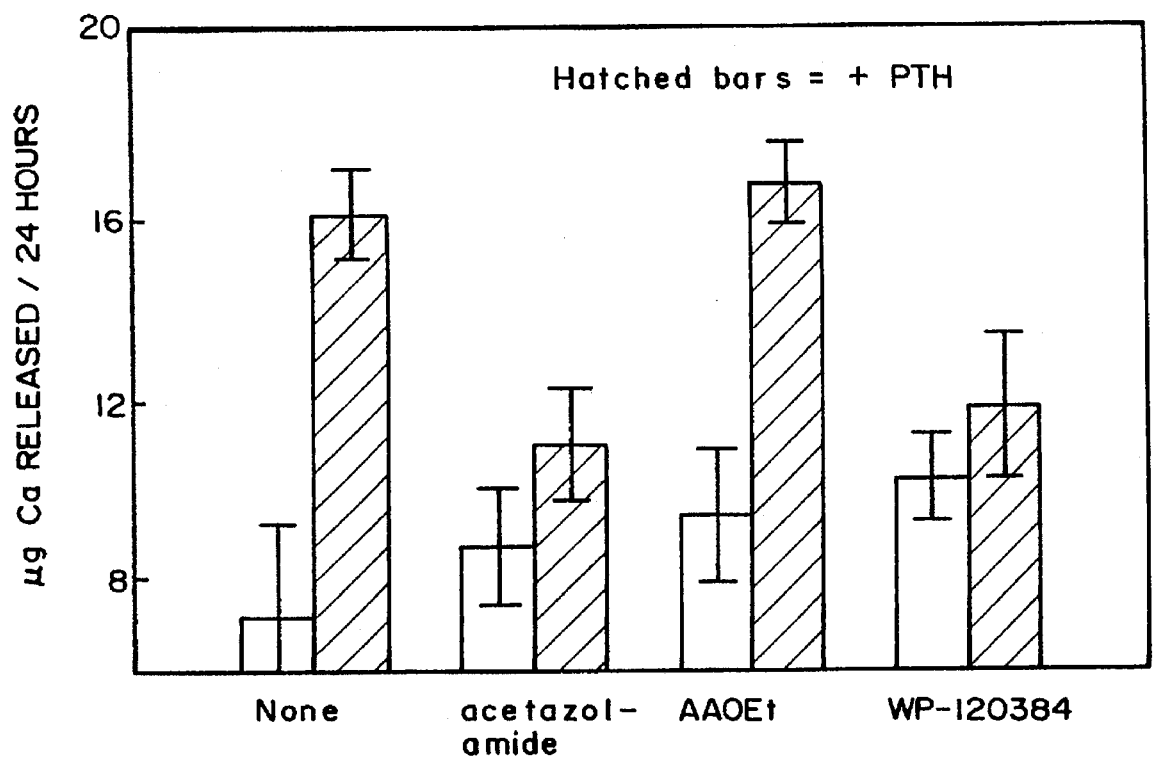
FIG. 3 is a graphic illustration depicting the effect of tetracycline, acetazolamide, AAOEt, and TIA on bone calcium release in rats.

1. In vitro inhibition of bone resorption. Rat calvaria were cultured as described. Some cultures include the addition of parathyroid hormone (PTH) in the presence and absence of test compounds ($10^{-5}$M). Results are shown in FIG. 3. Treatment with PTH led to a significant stimulation of the net release of calcium from cultured bone. None of the test compounds had a demonstrable effect on basal rates of calcium release. PTH-stimulated calcium release from calvaria was inhibited by acetazolamide and TIA. Tetracycline is without effect at this concentration.

2. In vivo Inhibition of Bone Resorption a. The Induced Secondary Hyperparathyreid Rat.

In order to test the biological activity of TIA, the Induced Secondary Hyperparathyroid Rat (ISHR) model was employed. In this animal model and under the experimental conditions described above, TIA attenuated the developing hypercalcemia. Preliminary data are summarized in Table 2 below.

TABLE 2

| Treatment | Blood Calcium mg/dl |
|---|---|
| Prenephrectomy | 10.1 ± 0.3 |
| control (vehicle treated) | 12.2 ± 0.4 |
| acetazolamide (0.2 mol/kg) | 12.6 ± 0.2 |
| tetracycline (0.2 mol/kg) | 11.8 ± 0.4 |
| TIA (0.2 mol/kg) | 10.2 ± 0.5** |

**Different from control ($P \leq 0.05$)

These preliminary data indicate that the only effective agent under the described experimental conditions was TIA.

Acetazolamide, which would have antagonized the hypercalcemic response if given at the time of nephrectomy, was not effective when administered 24 hours prior to nephrectomy. This is not surprising since the half-life of acetazolamide is approximately 50 minutes in kidney intact animals. Although tetracycline, at high concentrations, typically inhibits PTH in vitro, it does not appear to be effective in this model. TIA given 24 hours prior to nephrectomy prevented the expected elevation of plasma calcium concentrations 4 hour after nephrectomy. Thus, TIA is effective under conditions where neither of its constituent parts is effective. This appears to indicate that the drug is stored in the body much longer than acetazolamide, which is a known inhibitor of bone resorption. It may also indicate that acetazolamide, or an active inhibitor of bone resorption is released subsequent to storage.

b. Classical endocrine ablation/replacement model

Parathyroid hormone was administered to parathyroidectomized rats who had received no food for 12 hours before PTH injection, to minimize gut calcium absorption. In an attempt to attenuate the developing increase in plasma calcium, TIA was administered 24 hours prior to PTH injection. The data are summarized below in Table 3 and again indicated that TIA may be an active inhibitor of PTH-stimulated calcium release from bone.

TABLE 3

| | Blood Calcium (mg/dL) | |
|---|---|---|
| Treatment | Before PTH | 6 hours post-treatment |
| Control (vehicle) | 5.2 ± 0.3 | 5.5 ± 0.2 |
| PTH | 5.2 ± 0.3 | 7.2 ± 0.2** |
| TIA | 5.9 ± 0.2 | 5.8 ± 0.2 |
| PTH + TIA | 5.3 ± 0.2 | 6.6 ± 0.2* |

**Significantly different from Control ($p < 0.05$)
*Significantly different from Control and PTH ($p < 0.05$)

In this model, TIA pretreatment decreased the PTH-induced increase in plasma calcium. This 33% inhibition of the calcemic response to PTH indicates the inhibition of the osseous response to PTH, while the renal response to the hormone remains intact, and also demonstrates that TIA would not be expected to alter renal reabsorption of calcium. From past work it is known that acetazolamide is not effective in this model, yet TIA is effective. Acetazolamide is not effective in this model because this drug produces a metabolic acidosis. TIA is effective because of its high affinity for bone and the lack of an acidotic response.

EXAMPLE II

TIE (WP-021786)

a) Synthesis

TIE was synthesized using the same scheme as for TIA, except starting with ethoxzolamide in lieu of acetazolamide, as shown below.

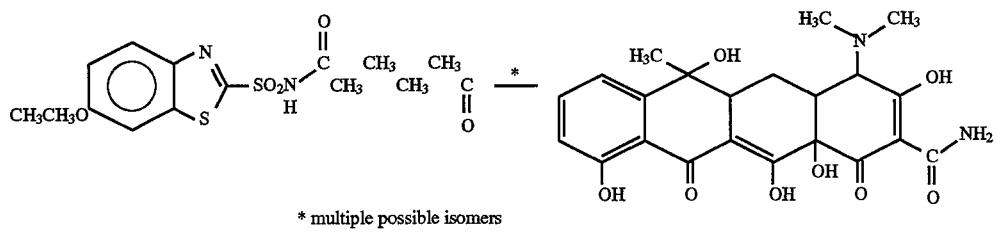

\* multiple possible isomers

TIE

To a 500 mL round bottom flask was added 3.87 mmol ethoxzolamide (6-ethoxybenzothiazolesulfonamide) and 50 mL of freshly dried $Na_2SO_4$) pyridine. This mixture was slurried with vigorous stirring, and 3.87 mmol adipoyldichloride was added dropwise to the slurry. The resulting mixture was then heated to 50° C., then external heating was removed. The exothermic reaction took the pot temperature to 91° C. over about 30 minutes, then the temperature decreased. Chromatographic analysis showed no remaining ethoxzolamide. At this point, 3.87 mmol of tetracycline was added, and temperature was maintained at 60° C. for four hours. Two mL of methanol was added to scavenge any remaining acyl chloride. Product was purified by hydroxyapatite chromatography. The final product was a yellow powder which was found to be pure as assessed by reverse phase HPLC. Yield in this instance was 23%.

b) Physicochemical studies

UV-visible spectroscopy was performed on solutions of TIE, tetracycline and ethoxzolamide. TIE retained spectral characteristics of the parent compounds. Data obtained are shown in Table 4.

TABLE 4

| Compound | Solvent | lambda$_{max}$ | Molar extinction coefficient |
|---|---|---|---|
| TIE | water | 360 | 14,340 |
| | | 272 | 16,980 |
| TIE | 0.1 M NaOH | 380 | 15,800 |
| | | 282 | 14,700 |
| | | 245 | 17,900 |
| TIE | 0.1 M HCl | 355 | 12,500 |
| | | 260 | 17,300 |
| tetracycline | water | 359 | 15,100 |
| | | 274 | 14,640 |
| tetracycline | 0.1 M NaOH | 384 | 16,700 |
| | | 282 | 12,000 |
| | | 262 | 14,200 |
| tetracycline | 0.1 M HCl | 357 | 15,040 |
| | | 267 | 19,060 |
| ethoxzolamide | water | 302 | 5,400 |
| | | 253 | 3,400 |
| ethoxzolamide | 0.1 M NaOH | 292 | 5,300 |
| | | 254 | 4,100 |
| ethoxzolamide | 0.1 M HCl | 306 | 5,400 |
| | | 255 | 3,600 | c) Biochemical Properties

Biochemical properties of TIE were examined. TIE did not bind to hydroxyapatite (used in purification), remained bound even when washed with hot water or organic solvents, and was eluted by 2M phosphate buffer at pH 7. TIE was completely inactive as a CA inhibitor, and hydrolysis (under either acidic or basic conditions) yielded a CA inhibitor which co-chromatographed with ethoxzolamide.

d) Assessment of Biological Activity

Figure 4:
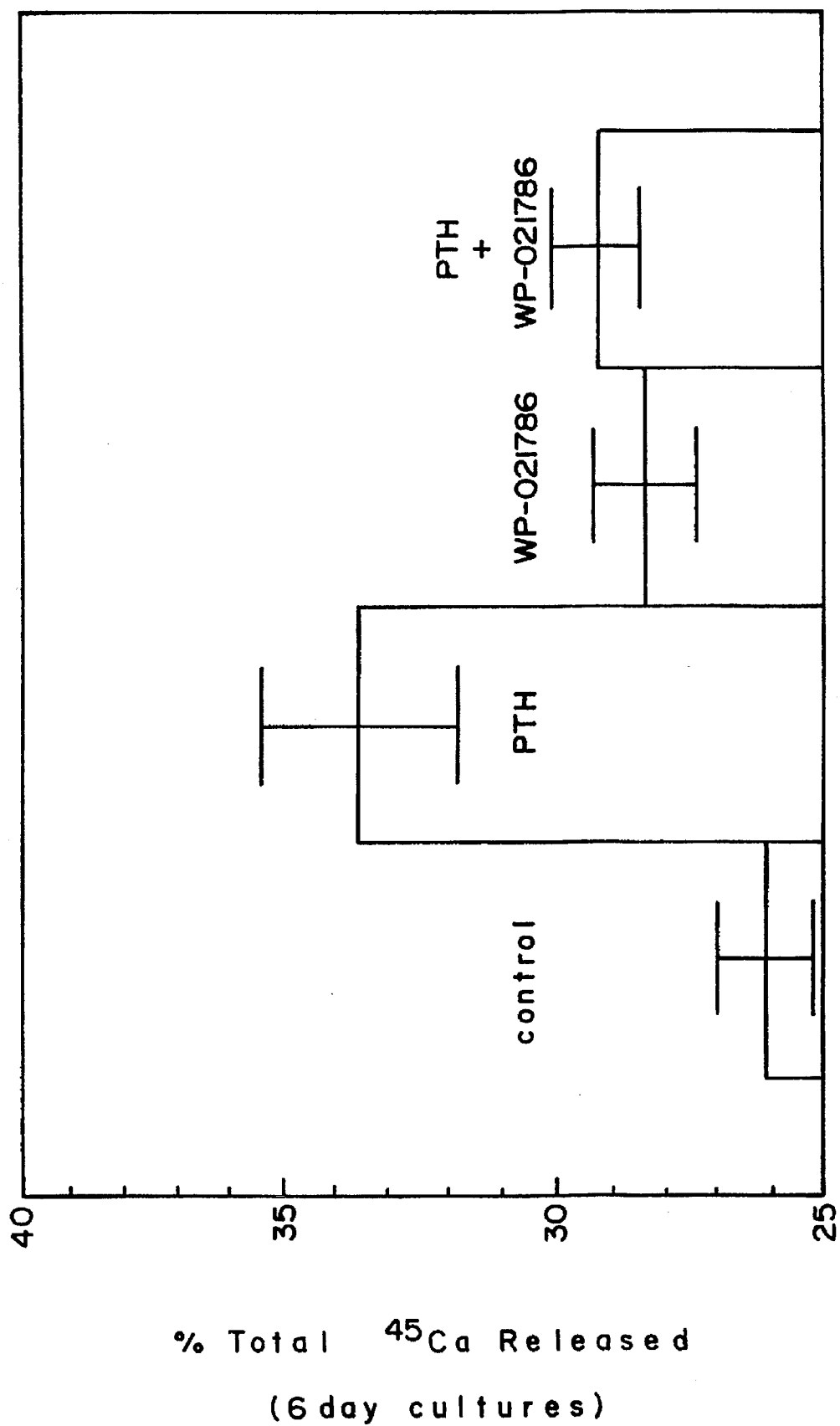
FIG. 4 is a graphical illustration depicting the effect of tetracycline internally active ethoxzolamide (TIE or WP-021786) on bone calcium release in rats.

The ability of TIE to attenuate bone resorption was investigated in the in vitro organ culture system, using calvaria from rat pups which had been radiolabeled with $^{45}Ca$ in utero. Data shown in FIG. 4 indicates that inclusion of 10 uM TIE in these cultures inhibits PTH stimulated calcium release.

EXAMPLE III

TAA (KK-02087)

a) Synthesis

The remaining compounds disclosed (Examples III–VI) are synthesized such that the "Active" configuration (primary sulfonamide is preserved. In order to accomplish this a thiadiazole with a useful functional group was prepared. The precursor thiadiazole used is 2-amino-1,3,4-thiadiazole-5-sulfonamide (WP-061786). This was prepared by hydroylsis of the acetamido function of acetazolamide as shown below.

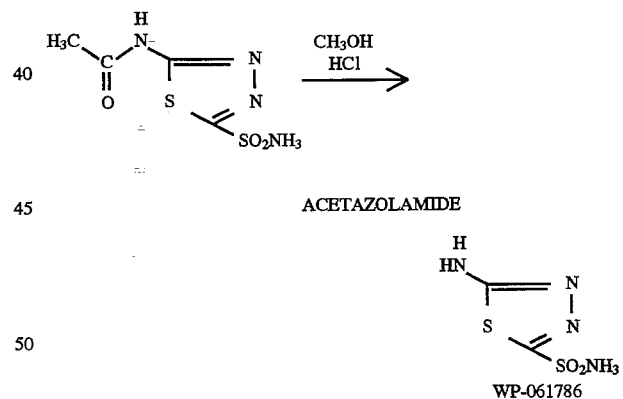

In a 2 L round bottom flask, 0.2 mol acetazolamide was slurried in 600 mL methanol and 60 mL 12N HCl. The mixture was heated to reflux and held for four hours, at which time the milky slurry became a true solution (water white). Ten more mL of HCl were added and reaction progress monitored by TLC and HPLC. Yields were usually 95+% with a purity greater than 99%. Physicochemical properties of this precursor are summarized in Table 5.

TABLE 5

| COMPOUND | lambda$_{max}$ nm (a) | k' (b) | Solubility pH = 7.6 (mM) | ether:buffer partition coefficient (pH = 7.6) | Potency as CA inhibitor (%) |
|---|---|---|---|---|---|
| acetazolamide | 266 | 2.13 | 6.7 | 0.20 | 100 |
| WP-061786 | 280 | 0.39 | 28.4 | 0.15 | 20 | a - UV-visible spectrophometry
b - HPLC capacity factor

For synthesis of TAA, 10 ml of the precursor thiadiazole (WP-061786) was mixed into 800 mL dry tetrahydrofuran (THF). To this was added one equivalent of dry pyridine and (dropwise, 1 mL/min) one equivalent of adipoyldichloride. Reaction (at room temperature) progress was monitored using TLC. After all of the precursor thiadizole was consumed, one equivalent each of tetracycline and pyridine were added. After 24 hours, excess pyridine and methanol were added, and the reaction mixture was purified using silica gel chromatography.

b) Physicochemical Properties

Figure 5:
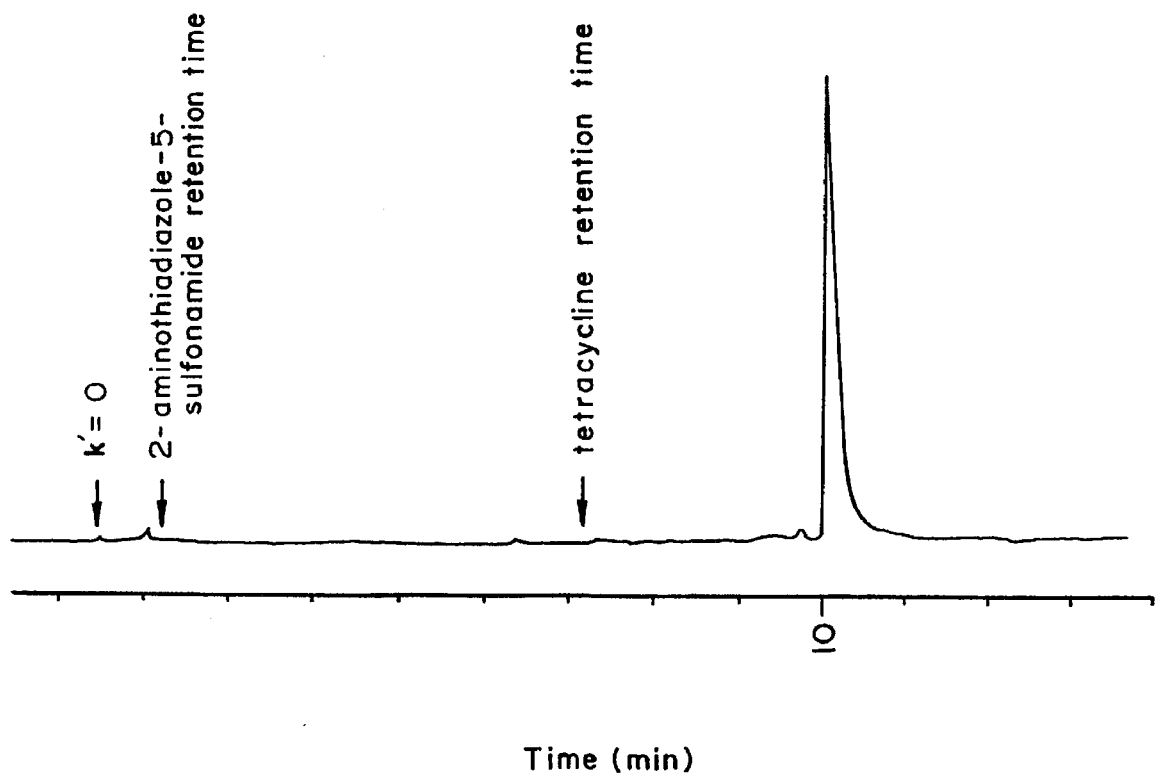
FIG. 5 is a graphical illustration depicting the results of reverse phase high performance liquid chromatography of tetracycline active acetazolamide after its preparation.
Figure 6:
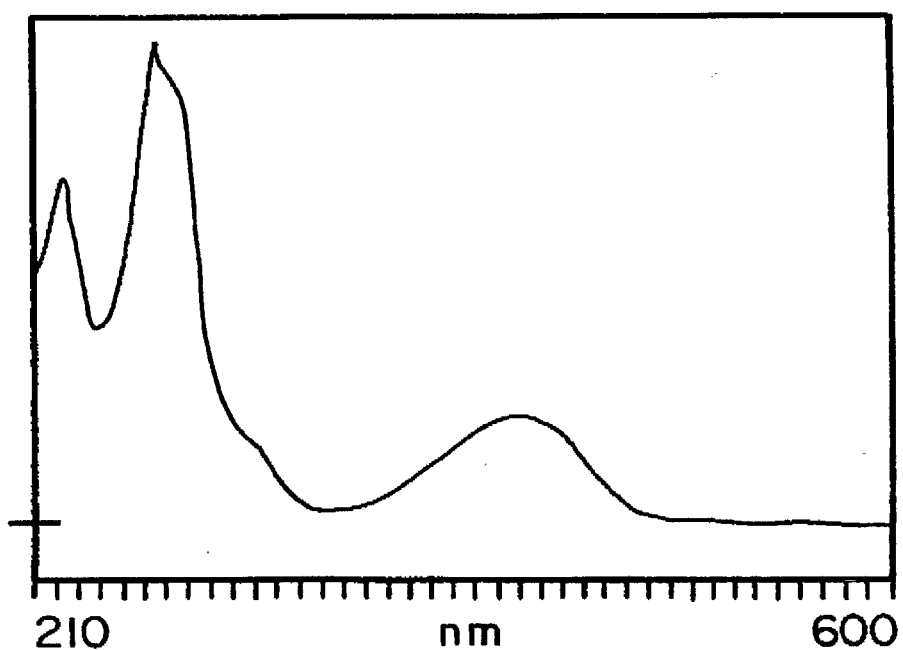
FIG. 6 is a graphical illustration depicting an ultraviolet-visible absorption spectrum for tetracycline-active-acetazolamide.

FIG. 5 is a reverse phase high performance liquid chromatogram of the final product, demonstrating its purity and distinct solubility difference from the parent compounds. FIG. 6 is a UV-visible absorption spectrum for TAA. The chemical structure of TAA is demonstrated below.

EXAMPLE IV

TAE (WP-050686)

a) Synthesis

Figure 7:
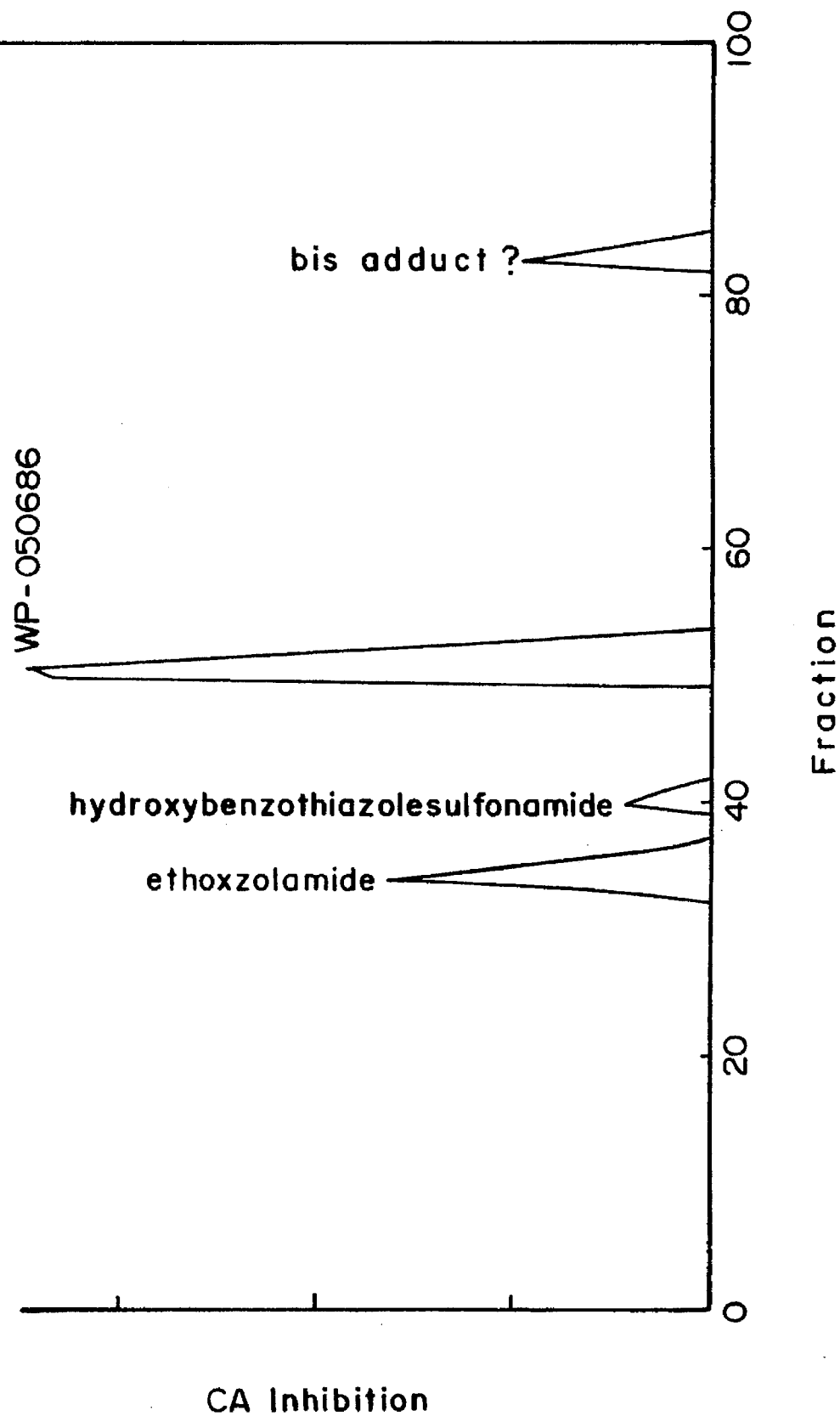
FIG. 7 is a graphical illustration depicting the results of a reverse phase preparative chromatography performed on tetracycline active-ethoxzolamide Δ1 (TAE-1 or WP-050686).

The benzothiazole precursor used to synthesize this compound was 6-hydroxybenzothiazolesulfonamide. The scheme for synthesis is similar to the one described by Schoenwald, et al., *J. Med. Chem.* 27: 810–812 (1984). To produce TAE-1, 1 mmol of the benzothiazole precursor was dissolved in 100 mL of acetone. To this was added a mixture of 5 mmol each of adipic acid and dicyclohexylcarbodiimide. The mixture was heated to reflux and held for a total of 48 hours. Purification was accomplished by hydroxyapatite chromatography. Finally, reverse phase preparative chromatography (FIG. 7) was performed to assure resolution of

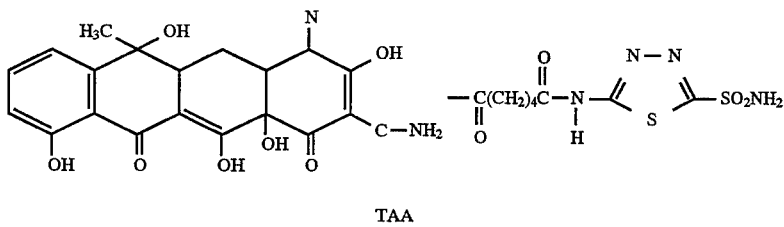

TAA c) Biochemical Studies

TAA was tested as a carbonic anhydrase inhibitor and has a K$_I$ of 180 nM. This compound and has the requisite affinity for hydroxyapatite, as shown in Table 6.

TAE-1 from other CA inhibitors. The yield from this scheme was only about 1%. The chemical structure of TAE-1 is shown below.

TABLE 6

| Compound | % Bound to Hydroxyapatite |
|---|---|
| 1. WP-061786 (precursor) | -0- |
| 2. Tetracycline | 85 |
| 3. KK-020286 (TAA) | 86 |

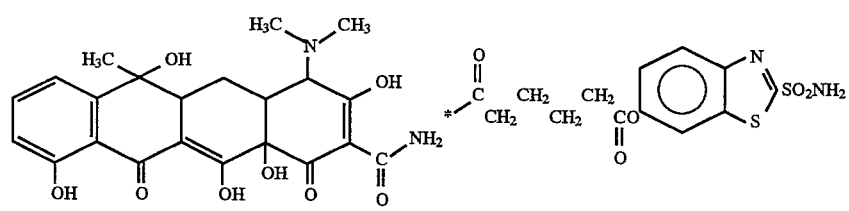

* multiple possible isomers

TAE-1 b) Assessment of Biological Activity

Figure 8:
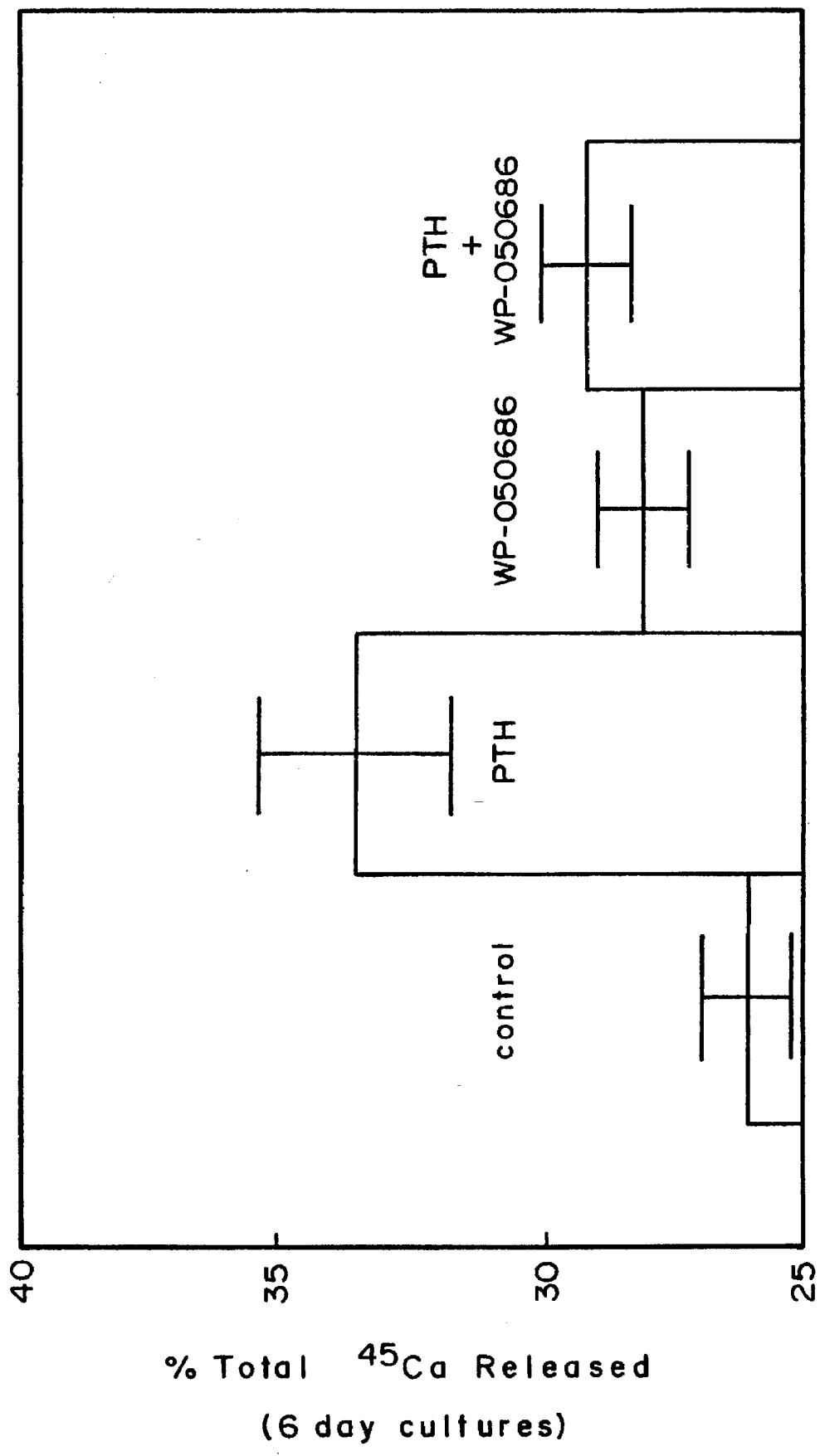
FIG. 8 is a graphical illustration depicting the effect of TAE-1 on calcium release in rats.

Pharmacological testing in the in vitro calvarial organ culture system demonstrated that TAE-1 attenuates PTH-stimulated bone resorption (FIG. 8).

EXAMPLE V

TAE-2 (WP-020387)

a) Synthesis

The low yield for the TAE-1 synthesis described in Example IV was apparently due to the action of the carbodiimide on the carboxamide of tetracycline, namely the dehydration of this function to the corresponding nitrile. Such a product would not have great affinity for calcium and would be selected against in the purification scheme. To improve yield, a different strategy was employed to produce an epoxy-activated benzothiazole which would then react with tetracycline as shown below.

using hydroxyapatite chromatography to yield 10 mg product (7.8% of theo.).

b) Biochemical Studies and Biological Activity

Figure 9:
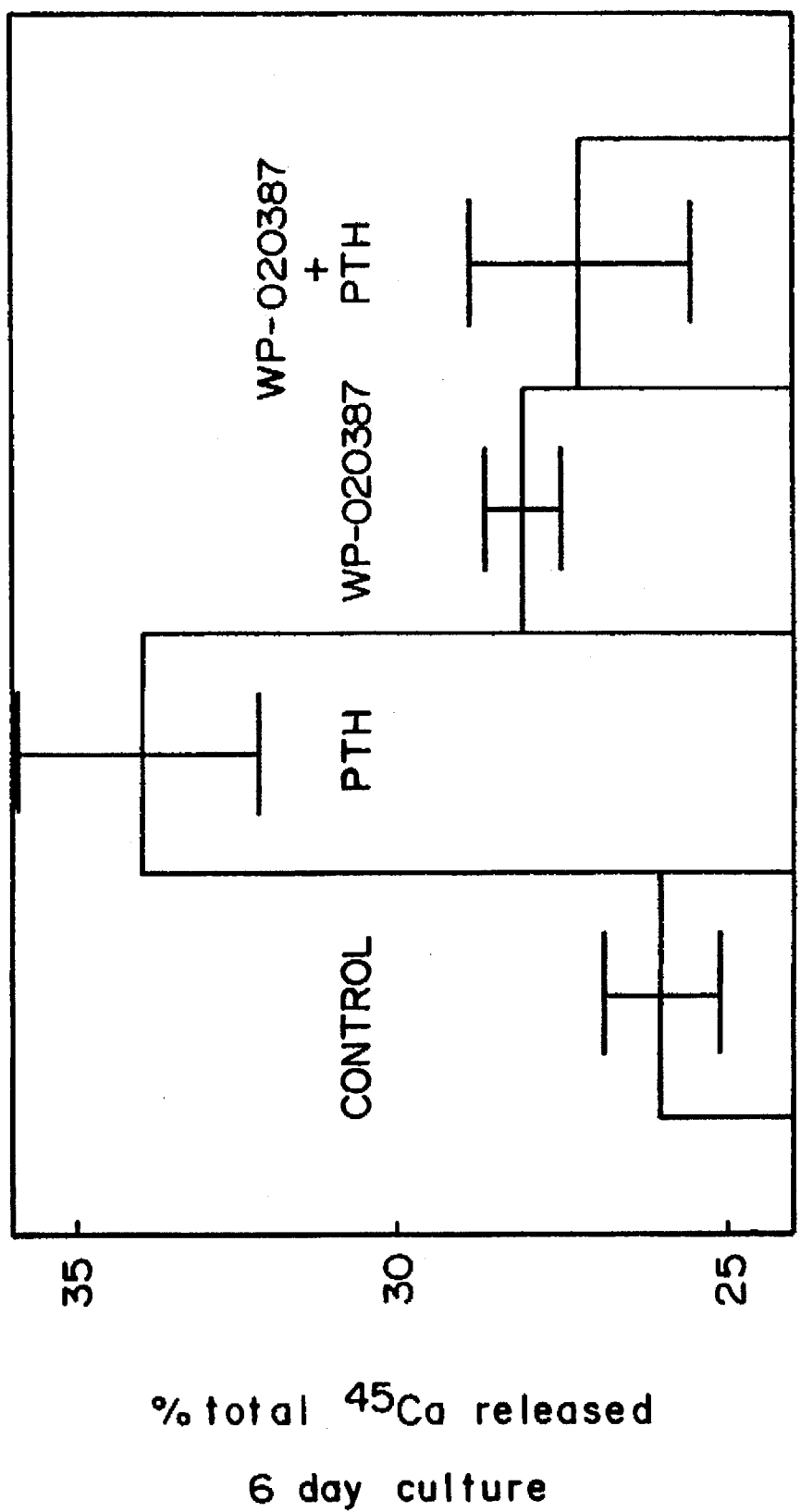
FIG. 9 is a graphical illustration of the effect of tetracycline active ethoxzolamide Δ-2 (TAE-2 or WP-020387) on calcium release in rats.
Figure 10:
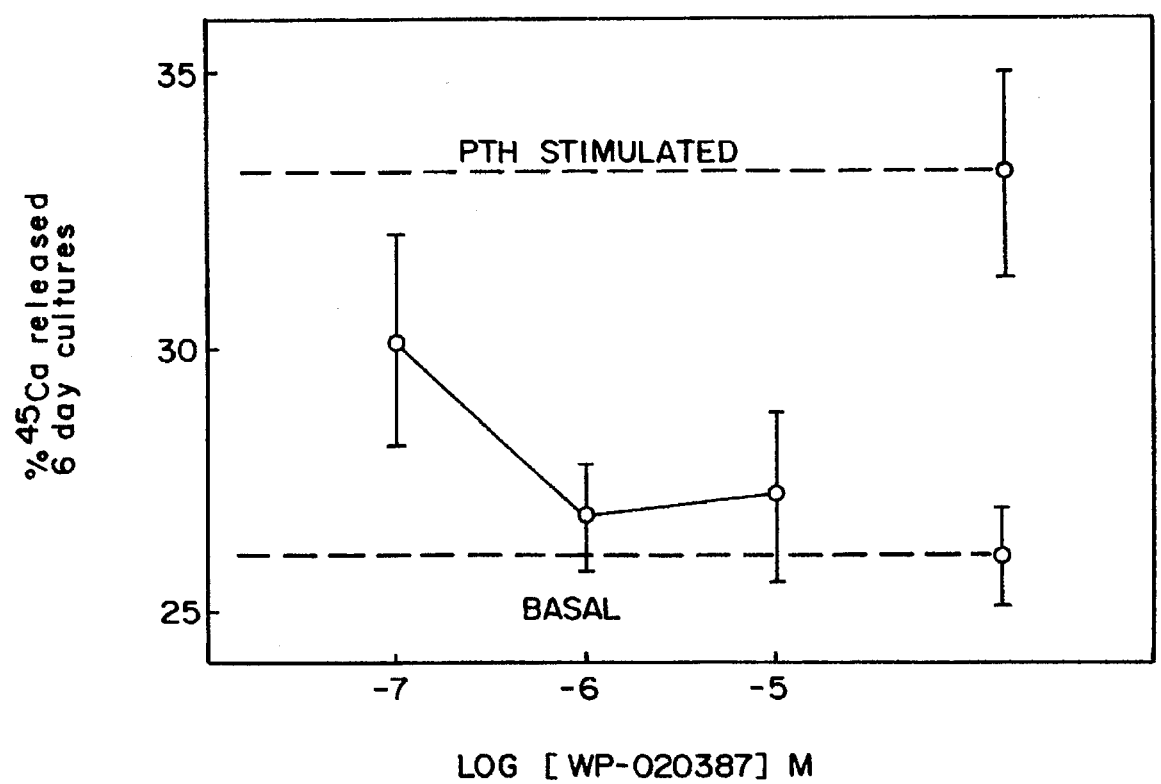
FIG. 10 is a graphical illustration of the concentration effect of TAE-2 on calcium release in rats.

TAE-2 was evaluated as a carbonic anhydrase inhibitor and has a $K_I$ of nM. In addition, TAE-2 attenuates PTH stimulated calcium release from calvaria in culture (FIG. 9) in a concentration dependent fashion (FIG. 10).

EXAMPLE VI

PAA (WP-050188)

a) Synthesis

PAA is an adduct of thiadiazolesulfonamide and a biphosphonate such that the product is an active inhibitor. The chemical structure of PAA is shown below.

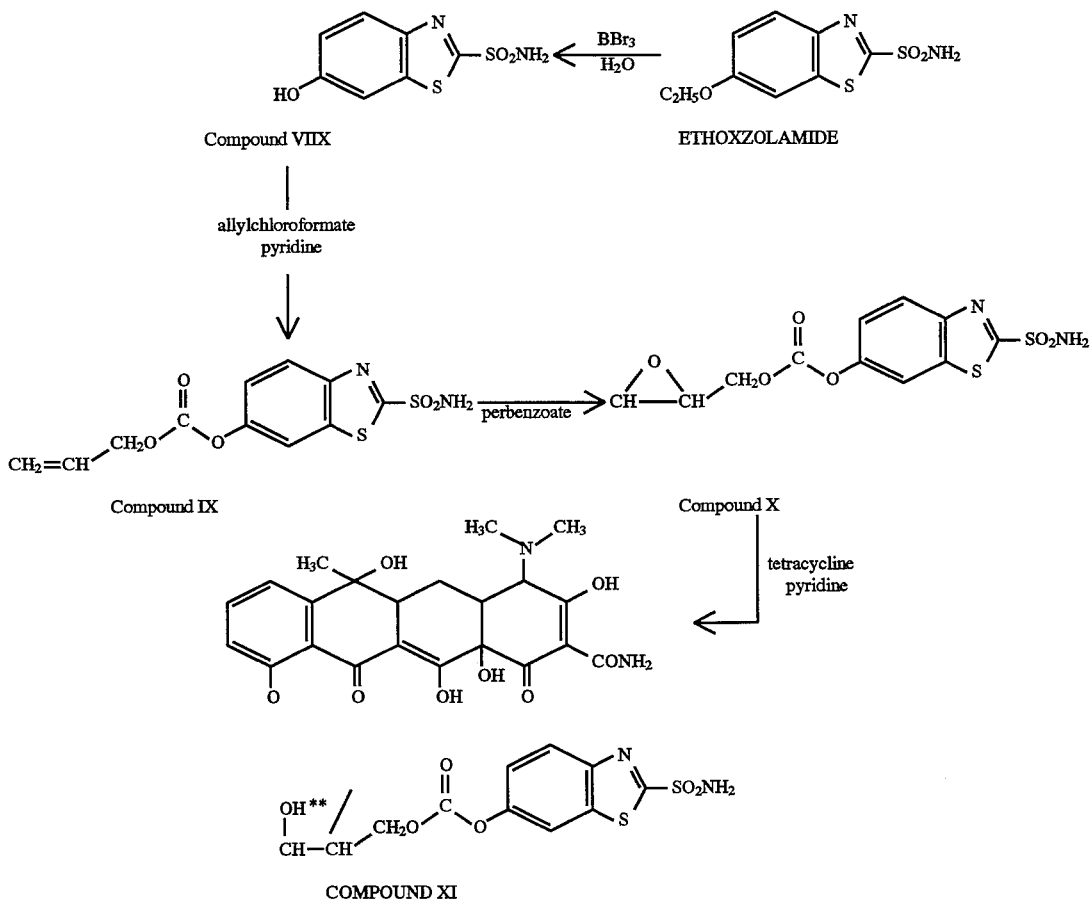

20 mmol of hydroxybenzothiazolesulfonamide was dissolved in 50 mL THF. To this was added a solution of 20 mmol allylchloroformate and 22 mL of pyridine in 50 mL THF. The exothermic reaction increased the temperature of the mixture to 42°. After four hours, the pot mixture is poured into a liter of ice cold water and extracted into ethyl acetate. Solvent was stripped under vacuum and the product recrystallized from hot water. Yield=22%. This allyl derivative was treated with m-chloroperbenzoic acid in THF for 18 hours, the solvent was stripped and the residue extracted with dichloromethane. Finally, the oxirane derivative (75 mg) was mixed with equimolar tetracycline and pyridine, and heated to 60° for 8 hours. Purification was accomplished

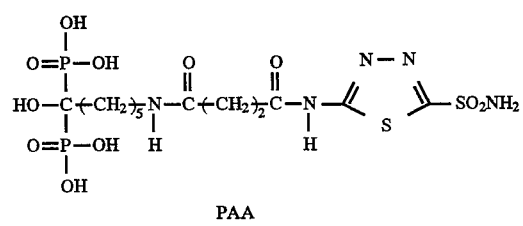

Figure 11:
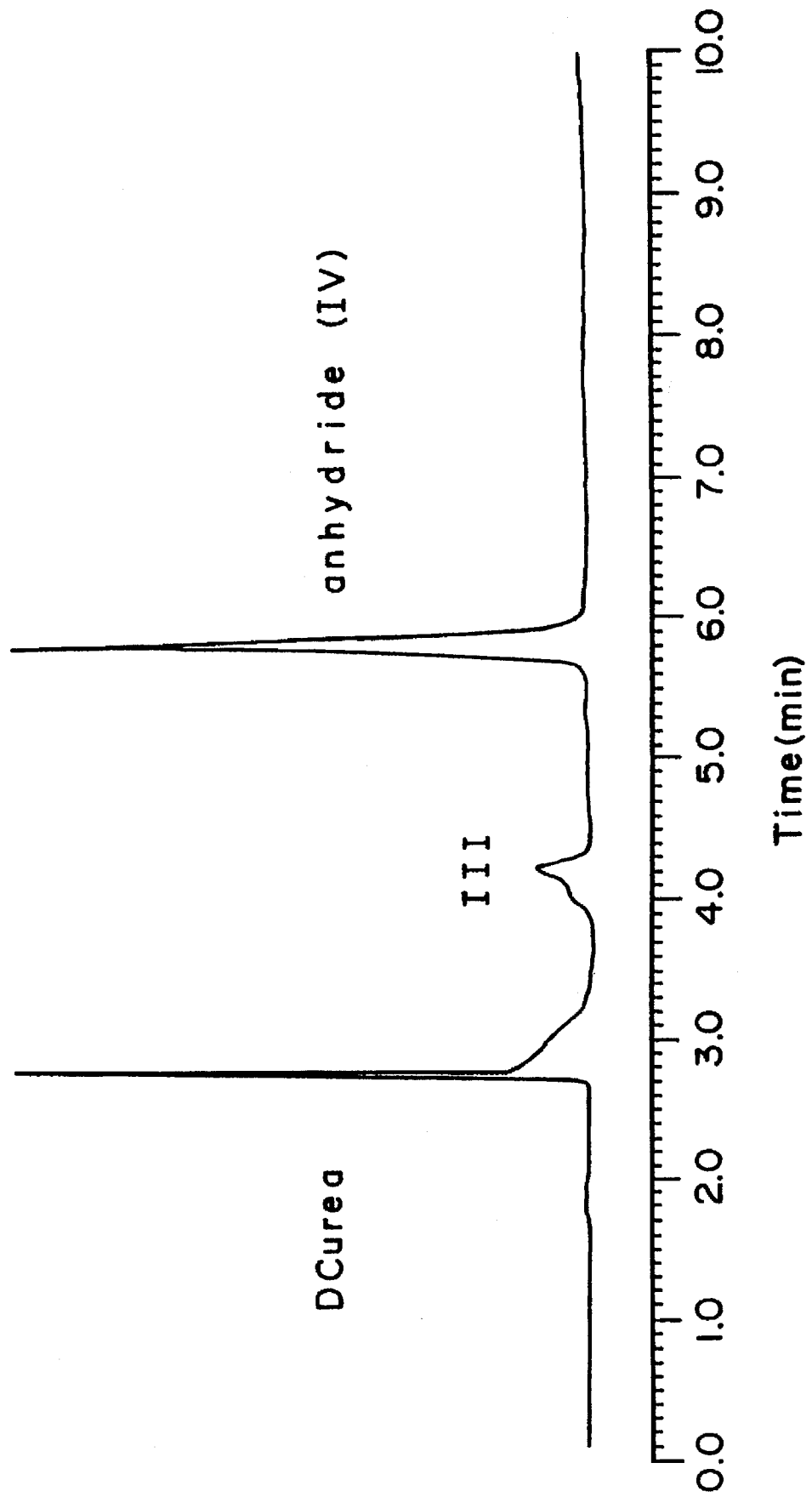
FIG. 11 is a graphical representation of the results of a chromatogram of succinylazolamide (III), anhydride (IV), and DC urea.

Aminothiadizolesulfonamide (I) was heated with succinic anhydride (II) to form succinylazolamide (III). The numbers in parentheses refer to FIG. 11. Ten mmol of III was then dissolved in 200 mL THF, and 10 mmol dicyclohexylcarbodimide were added to form the anhydride (IV). The reaction proceeded to approximately 90% of completion (FIG. 11). The dicyclohexylurea formed was filtered, and the product was recovered after stripping the THF under reduced pressure.

Figure 12:
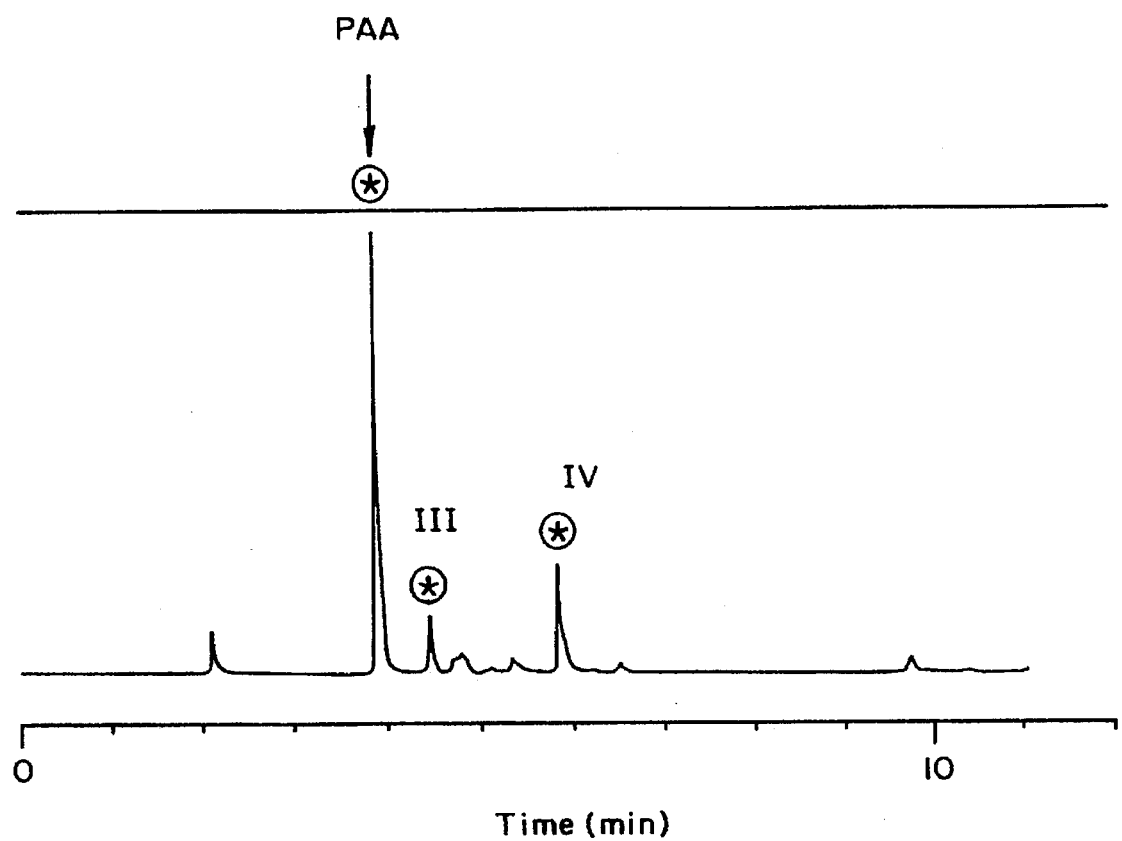
FIG. 12 is a graphical representation of the results of a chromatogram (HPLC reverse phase) of aminohexyldiphosphonate-active-acetazolamide (PAA or WP-050188) before purification.
Figure 13:
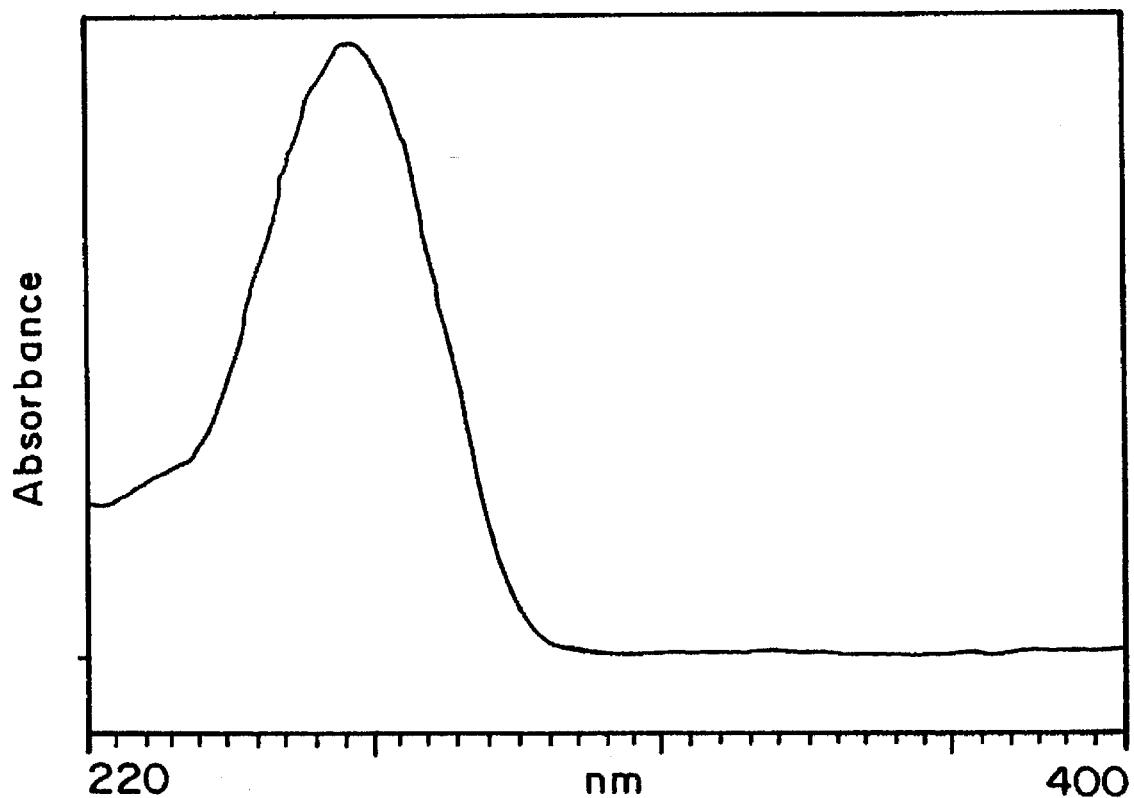
FIG. 13 is a graphical illustration of the ultra-violet visible absorption spectrum of PAA.

One and one half grams of this anhydride were mixed with 2 grams of aminohexyldiphosphonate (V) and 5 grams of 1-(3-dimethylaminopropyl)-3-ethylcarbodiimide hydrochloride in 50% aqueous acetene at pH=8. After 24 hours, acetone was removed under reduced pressure and the product was purified using hydroxyapatite. The final residue was extracted into THF (to leave the bisphosphonate behind). A chromatogram (HPLC reverse phase) of the reaction mixture before purification (FIG. 12) showed the product, PAA, to be more water soluble than the parent thiadiazolesulfonamide. In addition, the UV-visible absorption spectrum (FIG. 13) demonstrates the characteristics of all of the members of this family. Also, PAA is an inhibitor of CA with a $K_I$ of 120 nM.

We claim:

1. A method for the treatment or prophylaxis of degenerative bone disorders in animals which comprises administering to the animal in need of such treatment an effective amount of a compound formed by:
   (a) reacting a bridging agent with an inhibitor of carbonic anhydrase under acylating conditions, said bridging agent being an alkylene chain having at one end a functional group capable of aromatic electrophilic substitution and at the other end an acylating group, said inhibitor of carbonic anhydrase being an heterocyclic sulfonamide, and
   (b) then reacting the product of (a) with a bone seeking agent under electrophilic aromatic substitution conditions, said bone seeking agent being a tetracycline and said compound having the ability to bind to bone mineral and to inhibit carbonic anhydrase.

2. A method for the treatment or prophylaxis of degenerative bone disorders in animals which comprises administering to the animal in need of such treatment an effective amount of a compound formed by:
   (a) reacting a bridging agent with an inhibitor of carbonic anhydrase under acylating conditions, said bridging agent being an alkylene chain having at both ends thereof an acylating group, said inhibitor of carbonic anhydrase being an heterocyclic sulfonamide; and
   (b) then reacting the product of (a) under acylating conditions with a bone seeking agent, said bone seeking agent being a diphosphonate and said compound having the ability to bind to bone mineral and to inhibit carbonic anhydrase.

3. The method of claim 1 wherein the functional group on the bridging agent capable of undergoing electrophilic aromatic substitution is a halide, hydroxy, olefin, or carboxy or acylating derivative of the carboxy.

4. The method according to claim 1 or 2 wherein the bridging agent is adipoyl dichloride.

5. The method of claim 1 or 2 wherein the sulfonamide is acetazolamide, methazolamide, ethoxzolamide or benzolamide.

6. The method of claim 1 wherein the tetracycline is chlortetracycline hydrochloride, demeclocyline hydrochloride, doxycycline, tetracycline, methacycline or oxytetracycline.

7. The method of claim 2 wherein the diphosphonate is aminohexyldiphosphonate, ethane 1-hydroxy-1, 1-diphosphonic acid, dichloromethane diphosphonic acid or 3-amino-1-hydroxypropane-1, 1-diphosphonic acid.

8. The method according to claim 1 wherein the osteostat is tetracycline-internally-active-acetazolamide, tetracycline-internally active-ethoxzolamide, tetracycline active acetazolamide, tetracycline active ethoxzolamide A1, or tetracycline active ethoxzolamide A2.

9. The method according to claim 1 or 2 wherein the bridging agent contains 4–20 carbon atoms.

10. A compound which is prepared by the process comprising:
    (a) reacting a bridging agent with an inhibitor of carbonic anhydrase under acylating conditions, said bridging agent being an alkylene chain having at one end thereof a functional group capable of aromatic electrophilic substitution and at the other end an acyl group capable of undergoing acylating reactions, said inhibitor of carbonic anhydrase being an heterocyclic sulfonamide and
    (b) reacting the product of (a) with a bone seeking agent under electrophilic aromatic substitution conditions, said bone seeking agent being a tetracycline, and said compound having the ability to bind to bone mineral and to inhibit carbonic anhydrase.

11. A compound prepared by the process comprising:
    (a) reacting a bridging agent with an inhibitor of carbonic anhydrase under acylating conditions, said bridging agent being an alkylene chain having at both ends an acylating group capable of undergoing acylating reactions and said inhibitor of carbonic anhydrase being an heterocyclic sulfonamide, and
    (b) reacting the product of (a) with a bone seeking agent under acylating conditions, said bone seeking agent being a diphosphonate, and said compound having the ability to bind to bone mineral and to inhibit carbonic anhydrase.

12. The compound according to claim 10 or claim 11 wherein the functional group on the bridging agent capable of undergoing electrophilic aromatic substitution is a halide, hydroxy, olefin, COOH or acylating derivative of the carboxy group.

13. The compound according to claim 10 or claim 11 wherein the bridging agent is adipoyl dichloride.

14. The compound according to claim 10 or claim 11 wherein the sulfonamide is acetazolamide, methazolamide, ethoxzolamide or benzolamide.

15. The compound according to claim 10 wherein the tetracycline is chlortetracycline hydrochloride, demeclocyline hydrochloride, doxycycline, tetracycline, methacycline or oxytetracycline.

16. The compound according to claim 11 wherein the diphosphonate is aminohexyldiphosphonate, ethane 1-hydroxy-1, 1-diphosphonic acid, dichloromethane diphosphonic acid or 3-amino-1-hydroxypropane-1, 1-diphosphonic acid.

17. The compound according to claim 10 or 11 wherein the bridging agent contains 4–20 carbon atoms.

18. The compound according to claim 10 wherein the compound is tetracycline-internally-active-acetazolamide, tetracycline-internally active-ethoxzolamide, tetracycline active acetazolamide, tetracycline active ethoxzolamide A1, or tetracycline active ethoxzolamide A2.

19. The compound according to claim 11 wherein the compound is amino hexyldiphosphate active acetazotamide.

20. The compound of claim 10 or 11 which is in association with a pharmaceutically acceptable carrier.

21. The method according to claim 2 wherein the compound is aminohexyldiphosphate-active acetazolamide.

* * * * *

UNITED STATES PATENT AND TRADEMARK OFFICE
CERTIFICATE OF CORRECTION

PATENT NO. : 5,641,762
DATED : June 24, 1997
INVENTOR(S) : William M. Pierce, Jr., et al.

It is certified that error appears in the above-identified patent and that said Letters Patent is hereby corrected as shown below:

In the Abstract, line 6: "inhibition" should read --inhibitor--
Column 1, line 8: "514,618" should read --514,638--
Column 1, line 48: "photeolytic" should read --proteolytic--
Column 2, lines 10 & 17: "acetazoramide" should read --acetazolamide--
Column 8, line 14: "chlorcbutanol" should read --chlorobutanol--
Column 10, line 56, "anhydase" should read --anhydrase--
Column 13, line 33: after "(theoretical)" insert --of--
Column 15, lines 18-19, "5X10-6M" should read --$5 \times 10^{-6}M$--
Column 15, line 47: "Hyperparathyreid" should read --Hyperparathyroid--
Column 24, line 61, Claim 19: "acetazotamide" shoudl read --acetazolamide--

Signed and Sealed this

Twenty-sixth Day of May, 1998

Attest:

BRUCE LEHMAN

Attesting Officer

Commissioner of Patents and Trademarks